(12) United States Patent
Reed et al.

(10) Patent No.: US 6,642,220 B1
(45) Date of Patent: Nov. 4, 2003

(54) COMPOUNDS THAT INHIBIT OESTRONE SULPHATASE; COMPOSITIONS THEREOF; AND METHODS EMPLOYING THE SAME

(75) Inventors: Michael John Reed, London (GB); Barry Victor Lloyd Potter, Bath (GB)

(73) Assignee: Sterix Limited, Oxford (GB)

( * ) Notice: Subject to any disclaimer, the term of this patent is extended or adjusted under 35 U.S.C. 154(b) by 0 days.

(21) Appl. No.: 09/319,213

(22) PCT Filed: Dec. 4, 1997

(86) PCT No.: PCT/GB97/03352

§ 371 (c)(1),
(2), (4) Date: Nov. 23, 1999

(87) PCT Pub. No.: WO98/24802

PCT Pub. Date: Jun. 11, 1998

Related U.S. Application Data

(63) Continuation-in-part of application No. 09/111,927, filed on Jul. 8, 1998, now Pat. No. 6,011,024.

(30) Foreign Application Priority Data

Dec. 5, 1996 (GB) .............................................. 9625334

(51) Int. Cl.[7] .............................................. A61K 31/56

(52) U.S. Cl. ..................................................... 514/182

(58) Field of Search .......................... 552/502; 514/182

(56) References Cited

U.S. PATENT DOCUMENTS

| | | | |
|---|---|---|---|
| 4,340,602 A | * | 7/1982 | Brooks ......................... 424/238 |
| 4,668,668 A | | 5/1987 | Brooks et al. |
| 4,937,237 A | | 6/1990 | Holt et al. |
| 5,281,587 A | | 1/1994 | Reed |
| 5,344,827 A | | 9/1994 | Reed |
| 5,604,215 A | | 2/1997 | Reed et al. |
| 5,616,574 A | * | 4/1997 | Reed et al. ................... 514/178 |
| 5,677,292 A | | 10/1997 | Li et al. |
| 5,705,495 A | * | 1/1998 | Schwarz et al. ............. 514/182 |
| 6,011,024 A | * | 1/2000 | Reed et al. ................... 514/171 |
| 6,187,766 B1 | * | 2/2001 | Reed et al. ................... 514/178 |
| 6,476,011 B1 | | 11/2002 | Reed et al. |

FOREIGN PATENT DOCUMENTS

| | | | |
|---|---|---|---|
| AU | 645975 | | 2/1994 |
| CA | 2196678 | | 2/1996 |
| DE | 114806 | | 8/1975 |
| DE | 44 29 398 A1 | | 2/1996 |
| DE | 4429398 | * | 2/1996 |
| EP | 0403185 | | 12/1990 |
| FR | 2133484 | | 12/1972 |
| GB | 1398026 | | 6/1975 |
| WO | WO 93/05064 | | 3/1993 |
| WO | 93/05064 | * | 2/1996 |

OTHER PUBLICATIONS

Purohit et al., Biochemistry vol. 34, No. 36, pp–11508–11514 (1995).
Haddow et al., Brit. Med. J., ii, 393, 4368–73 (1944).
Nathanson & Kelley, N. Eng. J. Med., 246, 135–145 (1952).
Ingle et al., (1981). N. Engl. J. Med., 304, 16–21.
Stewart et al., 1980. In: Breast Cancer: experimental and clinical aspects. Mouridsen and Palshof (eds). Oxford, Pergamon Press p83–88.
Elger et al., "Sulfamates of Various Estrogens are Prodrugs with Increased Systemic and Reduced Hepatic Estrogenicity at Oral Application," J. Steroid Biochem. Molec. Biol. vol. 55 No. 3/4, pp 395–403 (1995).
Purohit et al., "In vivo inhibition of oestrone sulphatase and dehydroepiandrosteroine sulphatase by oestrone–3–O–sulphamate," Int J. Cancer 63(1):106–11 (1995).
Elger et al., "Novel oestrogen sulfamates: a new approach to oral hormone therapy," Exp Opin Invest Drugs 7(4):575–89 (1998).
White et al., Principles of Biochemistry, Sixth Ed. 1978, p 311.
Hejaz et al., J. Mol. Chem., 1999, 42,3188–92.
Dorfman et al., Acta Endocrinol. 1966, 52, 619–26.
Woo et al., "Active Site Directed Inhibition of Estrone Sulfatase by Nonsteroidal Coumarin Sulfamates", J. Med. Chem., vol. 39, No. 7, Mar. 29, 1996, pp. 1349–1351.
Fishman et al., "Studies on the Directive O–Methylation of Catechol Estrogens", Journal of the American Chemical Society, vol. 89, No. 26, 1967, pp. 7147–7149.
Peters et al., "Analogues of [(Triethylsily)ethynyl]estradiol as Potential Antifertility Agents", Journal of Medicinal Chemistry, vol. 31, No. 3, 1988, pp. 572–576.

(List continued on next page.)

Primary Examiner—Barbara P. Badio
(74) Attorney, Agent, or Firm—Frommer Lawrence & Haug, LLP; Thomas J. Kowalski

(57) ABSTRACT

Disclosed and claimed are compounds suitable for use as an inhibitor of oestrone sulphatase in a subject in need thereof, as well as compositions containing such compounds and methods for using such compounds. Such compounds can be a sulphamate compound that has the Formula (X) and wherein X is a sulphamate group, and Y is $CH_2$ and optionally any other H attached directly to the ring system is substituted by another group (X)

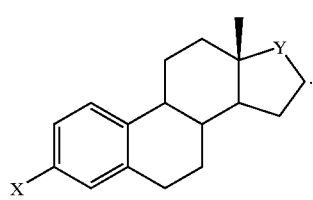

4 Claims, 6 Drawing Sheets

OTHER PUBLICATIONS

Rajan et al., "Estrogen Effects on NADH Oxidase and Superoxide Dismutase in Prepubertal Female Rats", Steroids, vol. 40, No. 6, 1982, pp. 651–660.

Cushman et al., "Synthesis, Antitubulin and Antimitotic Activity, and Cytotoxicity of Analogs of 2–Methyoxyestradiol, and Endogenous Mammalian Metabolite of Estradiol That Inhibits Tubulin Polymerization by Binding to the Colchicine Binding Site", Journal of Medicinal Chemistry, vol. 38, No. 12, Jun. 9, 1995, pp. 2041–2049.

Lovely et al., "2–(Hydroxyalkyl)estradiols: Synthesis and Biological Evaluation", Journal of Medicinal Chemistry, vol. 39, No. 9, Apr. 26, 1996, pp. 1917–1923.

Chemical Abstracts, vol. 107, No. 21, Nov. 23, 1987.

Townsley, J.D., "Further Studies on the Regulation of Human Placental Steroid 3–Sulfatase Activity", Endocrinology, vol. 93, No. 1, 1973, pp. 172–181.

Chemical Abstracts, vol. 068, No. 1, Jan. 1, 1968.

Schwarz et al., "Synthesis of Estrogen Sulfamates: Compounds with a Novel Endocrinological Profile", Steroids, vol. 61, No. 12, Dec. 1996, pp. 710–717.

Schwarz et al., Pharmazie, vol. 30 (1975), pp. 17–21.

Howarth et al., J. Med. Chem., vol. 37 (1994), pp. 219–221.

Zeitschrift Fur Chemie, vol. 14, No. 1, 1974 pp. 15–16.

Townsley et al., Research Steroids, vol. 5 (1973), pp. 73–78.

Erythrocytes as a drug carrier—Investigations with selected estrogens for loading following oral administration, Natural Science Faculty, Science, Council, Martin–Luther Unversitat Halle–Wittenberg, Germany, Aug. 1989 (hereinafter "the Claussen Dissertation").

"Animal Experimental Contribution to the Development of Estrogenic Substances" (hereinafter "the Stölzer Dissertation"), Dissertation for award of Doctor of Science degree at the Mathematic–Naturwissenschaftlichh–Technischen faculty of Friedrich–Schiller–University Jena, Jul. 1989.

* cited by examiner

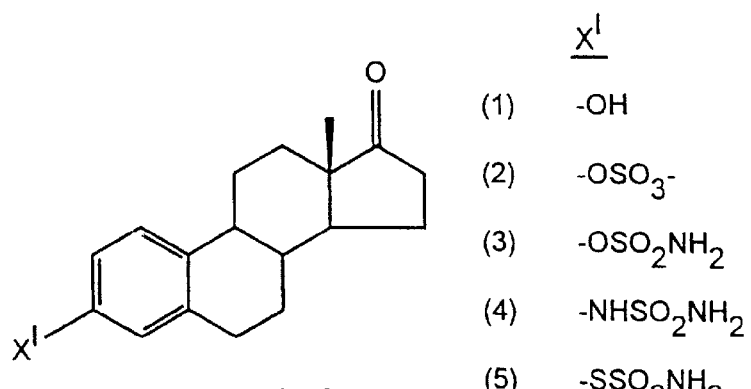
| | $X^I$ |
|---|---|
| (1) | -OH |
| (2) | $-OSO_3^-$ |
| (3) | $-OSO_2NH_2$ |
| (4) | $-NHSO_2NH_2$ |
| (5) | $-SSO_2NH_2$ |
FIG. 1
X - B - A    I
FIG. 2
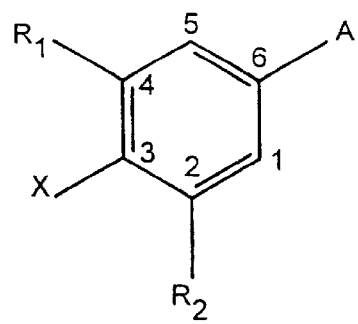
FIG. 3
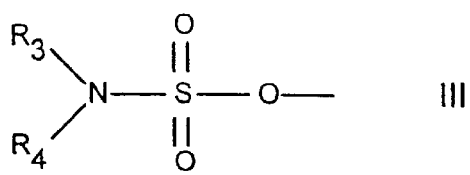
FIG. 4
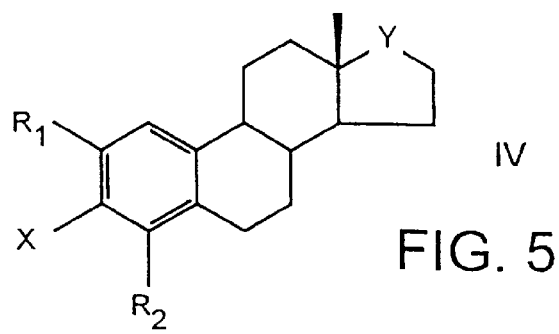
FIG. 5

COMPOUNDS THAT INHIBIT OESTRONE SULPHATASE; COMPOSITIONS THEREOF; AND METHODS EMPLOYING THE SAME

RELATED APPLICATIONS

This application is a 371 of PCT/GB97/03352 filed Dec. 4,1997 continuation-in-part of allowed U.S. application Ser. No. 09/111,927, filed Jul. 8, 1998, now U.S. Pat. No. 6,011,024, incorporated herein by reference; and, all documents cited in the following text, and in U.S. Ser. No. 09/111,927 are hereby incorporated herein by reference.

The present invention relates to a compound.

In particular the present invention relates to a compound and to a pharmaceutical composition comprising the compound.

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore specific inhibitors of oestrogen biosynthesis are of potential value for the treatment of endocrine-dependent tumours.

Over the past two decades, there has been considerable interest in the development of inhibitors of the aromatase pathway which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours[1,2] This theory is supported by a modest reduction of plasma oestrogen concentration in postmenopausal women with breast cancer treated by aromatase inhibitors, such as aminoglutethimide and 4hydroxyandrostenedione[3,4] and also by the fact that plasma E1S concentration in these aromatase inhibitor-treated patients remains relatively high. The long half-life of E1S in blood (10–12 h) compared with the unconjugated oestrogens (20 min)[5] and high levels of steroid sulphatase activity in liver and, normal and malignant breast tissues, also lend support to this theory[6]. PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE").

Some of the compounds disclosed in PCT/GB92/01587 are shown in FIG. 1.

It is known that EMATE is a potent E1-STS inhibitor as it displays more than 99% inhibition of E1-STS activity in intact MCF-7 cells at 0.1 mM. EMATE also inhibits the E1-STS enzyme in a time- and concentration-dependent manner, indicating that it acts as an active site-directed inactivator[7,8]. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol[8,9]. Also, there is now evidence to suggest that androstenediol may be of even greater importance as a promoter of breast tumour growth[10]. EMATE is also active in vivo as almost complete inhibition of rat liver E1-STS (99%) and DHA-STS (99%) activities resulted when it is administered either orally or subcutaneously[11]. In addition, EMATE has been shown to have a memory enhancing effect in rats[14]. Studies in mice have suggested an association between DHA-STS activity and the regulation of part of the immune response. It is thought that this may also occur in humans[15,16]. The bridging O-atom of the sulphamate moiety in EMATE is important for inhibitory activity. Thus, when the 3-O-atom is replaced by other heteroatoms (FIG. 1) as in oestrone-3-N-sulphamate (4) and oestrone-3-S-sulphamate (5), these analogues are weaker non-time-dependent inactivators[12].

Although optimal potency for inhibition of E1-STS may have been attained in EMATE, it is possible that oestrone may be released during sulphatase inhibition[8,12], and that EMATE and its oestradiol congener may possess oestrogenic activity[13].

The present invention seeks to provide novel compounds suitable for the inhibition of E1-STS but preferably wherein those compounds have no, or a minimal, oestrogenic effect.

According to a first aspect of the present invention there is provided a sulphanate compound suitable for use as an inhibitor of oestrone sulphatase, wherein the compound has the Formula I; wherein A is a first group; B is an aryl ring structure having at least 4 carbon atoms in the ring and wherein the ring B is substituted in at least the 2 position and/or the 4 position with an atom or group other than H; X is a sulphamate group; wherein group A and ring B together are capable of mimicking the A and B rings of oestrone; and wherein group A is attached to at least one carbon atom in ring B.

The term "mimic" as used herein means having a similar or different structure but having a similar functional effect. In otherwords, group A and ring B together of the compounds of the present invention are bio-isosteres of the A and B rings of oestrone.

A key advantage of the present invention is that the sulphamate compounds of the present invention can act as EL-STS inhibitors.

Another advantage of the compounds of the present invention is that they may be potent in vivo and that they may have less oestrogenic activity than the known compounds and can therefore be deemed to be a "non-oestrogenic compound". The term "non-oestrogenic compound" as used herein means a compound exhibiting no or substantially no oestrogenic activity.

The present invention therefore provides sulphamate compounds which may have a reduced oestrogenic activity.

Another advantage is that the compounds may not be capable of being metabolised to compounds which display or induce hormonal activity.

The compounds of the present invention are also advantageous in that they may be orally active.

The compounds of the present invention are further advantageous in that they may have an irreversible effect.

In a preferred embodiment, the-sulphamate compounds of the present invention are useful for the treatment of breast cancer.

In addition, the sulphamate compounds of the present invention are useful for the treatment of non-malignant conditions, such as the prevention of auto-immune diseases, particularly when pharmaceuticals may need to be administered from an early age.

The sulphamate compounds of the present invention are also believed to have therapeutic uses other than for the treatment of endocrine-dependent cancers, such as the treatment of autoimmune diseases.

Preferably, the sulphamate group is at position 3 of the ring B.

Preferably, the ring B has six carbon atoms in the ring.

Preferably, the compound has the Formula II; wherein X is the sulphamate group; A is the first group; $R_1$ and/or $R_2$ is a substituent other than H; wherein $R_1$ and $R_2$ may be the same or different but not both being H; and wherein optionally group A is attached to at least one other carbon atom in ring B.

Preferably, group A is additionally attached to the carbon atom at position 1 of the ring B.

Preferably, group A and ring B are a steroid ring structure or a substituted derivative thereof.

Preferably, the compound has the Formula IV; wherein X is the sulphamate group; $R_1$ and/or $R_2$ is a substituent other than H; wherein $R_1$ and $R_2$ may be the same or different but not both being H; and wherein Y is a suitable linking group.

Suitable linking groups for Y include groups made up of at least any one or more of C, O, N, and S. The linking groups can also comprise H. The linking group may also increase the size of the ring (i.e. the D ring). Preferably, however, the D ring comprising Y is a five-membered ring.

Preferably, Y is —$CH_2$— or —C(O)—.

Preferably, Y is —C(O)—.

Preferably, the compound has the Formula V; wherein X is the sulphamate group; $R_1$ and/or $R_2$ is a substituent other than H; and wherein $R_1$ and $R_2$ may be the same or different but not both being H.

The term "sulphamate" as used herein includes an ester of sulphamic acid, or an ester of an N-substituted derivative of sulphamic acid, or a salt thereof.

Preferably, the sulphamate group has the Formula III.

In Formula III, each of $R_3$ and $R_4$ is independently selected from H or a hydrocarbyl group.

The term "hydrocarbyl group" as used herein means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

In one preferred embodiment of the present invention, the hydrocarbyl group for the sulphamate group is a hydrocarbon group.

Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably, $R_3$ and $R_4$ are independently selected from H or alkyl, cycloalkyl, alkenyl and aryl, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R_3$ and/or $R_4$ is alkyl, the preferred On values are those where $R_3$ and $R_4$ are each independently selected from lower alkyl groups containing from 1 to 5 carbon atoms, that is to say methyl, ethyl, propyl etc. Preferably $R_3$ and $R_4$ are both methyl. When $R_3$ and/or $R_4$ is aryl, typical values are phenyl and tolyl (—$PhCH_3$; o-, m- or p-). Where $R_3$ and $R_4$ represent cycloalkyl, typical values are cyclopropyl, cyclopentyl, cyclohexyl etc. When joined together $R_3$ and $R_4$ typically represent an alkylene group providing a chain of 4 to 6 carbon atoms, optionally interrupted by one or more hetero atoms or groups, e.g. (—O— or —NH— to provide a 5-, 6- or 7-membered heterocycle, e.g. morpholino, pyrrolidino or piperidino.

Within the values alkyl, cycloalkyl, alkenyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl.

In some preferred embodiments, at least one of $R_3$ and $R_4$ is H.

In some further preferred embodiments, each of $R_3$ and $R_4$ is H.

Preferably, each of $R_1$ and $R_2$ is independently selected from H, l, cycloalkyl, alkenyl, aryl, substituted alkyl, substituted cycloalkyl, substituted alkenyl, substituted aryl, any other suitable hydrocarbyl group, a nitrogen containing group, a S containing group, a carboxy containing group.

Likewise, here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

Preferably, each of $R_1$ and $R_2$ is independently selected from H, $C_{1-6}$ alkyl, $C_{1-6}$ cycloalkyl, $C_{1-6}$ alkenyl, substituted $C_{1-6}$ alkyl, substituted $C_{1-6}$ cycloalkyl, substituted $C_{1-6}$ alkenyl, substituted aryl, a nitrogen containing group, a S containing group, or a carboxy group having from 1–6 carbon atoms.

Likewise, here within the values alkyl, cycloalkyl, alkenyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl.

Preferably, each of $R_1$ and $R_2$ is independently selected from H, $C_{1-6}$ alkyl, $C_{1-6}$ alkenyl, a nitrogen containing group, or a carboxy group having from 1–6 carbon atoms.

Preferably, each of $R_1$ and $R_2$ is independently selected from H, $C_{1-6}$ alkyl $C_{1-6}$ alkenyl, $NO_2$, or a carboxy group having from 1–6 carbon atoms.

Preferably, each of $R_1$ and $R_2$ is independently selected from H, $C_3$ alkyl, $C_3$ alkenyl, $NO_2$, or $H_3CO$.

Preferably, the compound is any one of the Formulae V–IX.

Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a K, value of less than 50 $\mu$mmolar when incubated with steroid sulphatase EC 3.1.6.2 at pH 7.4 and 37° C.

In another preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a $K_m$ value of less than 50 $\mu$molar when incubated with steroid sulphatase EC 3.1.6.2 at pH 7.4 and 37° C.

In a highly preferred embodiment, the compound of the present invention is not hydrolysable by an enzyme having steroid sulphatase (E.C. 3.1.6.2) activity.

Thus, the present invention provides novel sulphamate compounds.

Preferably the group A and the ring B together—hereinafter referred to as "group A/ring B combination"—will contain, inclusive of all substituents, a maximum of about 50 carbon atoms, more usually no more than about 30 to 40 carbon atoms.

A preferred group A/ring B combination has a steroidal ring structure, that is to say a cyclopentanophenanthrene skeleton. Preferably, the sulphamyl or substituted sulphamyl group is attached to that skeleton in the 3-position.

Thus, according to a preferred embodiment, the group A/ring B combination is a substituted or unsubstituted, saturated or unsaturated steroid nucleus.

A suitable steroid nucleus is a substituted (i.e. substituted in at least the 2 and/or 4 position and optionally elsewhere in the steroid nucleus) derivative of any one of: oestrone, 2-OH-oestrone, 2-methoxy-oestrone, 4-OH-oestrone, 6a-OH-oestrone, 7a-OH-oestrone, 16a-OH-oestrone, 16b-OH-oestrone, oestradiol, 2-OH-17b-oestradiol, 2-methoxy-17b-oestradiol, 4-OH-17b-oestradiol, 6a-OH-17b-oestradiol, 7a-OH-17b-oestradiol, 16a-OH-17a-oestradiol, 16b-OH-17a-oestradiol, 16b-OH-17b-stradiol, 17a-oestradiol, 17b-oestradiol, 17a-ethinyl-17b-oestradiol, oestriol, 2—OH-oestriol, 2-methoxy-oestriol, 4-OH-oestriol, 6a-OH-oestriol, 7a-OH-oestriol, dehydroepiandrosterone, 6a-OH-dehydroepiandrosterone, 7a-OH-dehydroepiandrosterone, 16a-OH-dehydroepiandrosterone, 16b-OH-dehydroepiandrosterone.

In general terms the group A/ring B combination may contain a variety of non-interfering substituents. In particular, the group A/ring B combination may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkenyl, e.g. ethenyl, or halogen, e.g. fluoro substituents.

The group A/ring B combination may even be a non-steroidal ring system.

A suitable non-steroidal ring system is a substituted (i.e. substituted in at least the 2 and/or 4 position and optionally elsewhere in the ring system) derivative of any one of: diethylstilboestrot, stilboestrol.

When substituted, the N-substituted compounds of this invention may contain one or two N-alkyl, N-alkenyl, N-cycloalkyl or N-aryl substituents, preferably containing or each containing a maximum of 10 carbon atoms.

When $R_1$ and/or $R_2$ and/or $R_3$ and/or $R_4$ is alkyl, the preferred values are those where each of $R_1$ and $R_2$ and $R_3$ and $R_4$ is independently selected from lower alkyl groups containing from 1 to 6 carbon atoms, that is to say methyl, ethyl, propyl etc.

When $R_1$ and/or $R_2$ and/or $R_3$ and/or $R_4$ is aryl, typical groups are phenyl and tolyl (—$PhCH_3$; o-, m- or p-).

Where $R_1$ and/or $R_2$ and/or $R_3$ and/or $R_4$ represent cycloalkyl, typical values are cyclopropyl, cyclopentyl, cyctohexyl etc.

When joined together $R_3$ and $R_4$ typically represent an alkylene group providing a chain of 4 to 6 carbon atoms, optionally interrupted by one or more hetero atoms or groups, e.g. —O— or —NH— to provide a 5-, 6- or 7-membered heterocycle, e.g. morpholino, pyrrolidino or piperidino.

Within the values alkyl, cycloalkyl, alkenyl and aryl we include substituted groups containing as substituents therein one or more groups which do not interfere with the sulphatase inhibitory activity of the compound in question. Examples of non-interfering substituents include hydroxy, amino, halo, alkoxy, alkyl and aryl.

We have also surprisingly found that when the compound has the Formula IV where Y=—$CH_2$— it is not necessary for the compound to be substituted in the 2 and 4 ring positions, ie $R_1$ and $R_2$ may both be hydrogen. In one embodiment of this aspect, any of the ring positions (including $R_1$ and $R_2$, but excluding Y) may be substituted.

Thus, according to another aspect of the present invention there is provided a sulphamate compound suitable for use as an inhibitor of oestrone sulphatase wherein the compound has the Formula X and wherein X is a sulphamate group, and Y is $CH_2$ and optionally any other H attached directly to the ring system is substituted by another group.

X may be as described above.

Any replacement for H on the ring system may be any one of the substituents described above in relation to $R_1$ and $R_2$.

In an especially preferred embodiment there is no substitution on the ring system, ie a compound of Formula IV where Y is —$CH_2$— and $R_1$ and $R_2$ are both H.

According to a second aspect of the present invention there is provided a sulphamate compound according to the present invention for use as a pharmaceutical.

According to a third aspect of the present invention there is provided a sulphamate compound according to the present invention for inhibiting oestrone sulphatase.

According to a fourth aspect of the present invention there is provided a pharmaceutical composition comprising a sulphamate compound according to the present invention; and a pharmaceutically acceptable carrier, excipient, adjuvant or diluent.

According to a fifth aspect of the present invention there is provided the use of a sulphamate compound according to the present invention in the manufacture of a pharmaceutical for inhibiting oestrone sulphatase.

The sulphamate compounds of the present invention may be prepared by reacting an appropriate alcohol with a sulfamoyl chloride, $R_3R_4NSO_2Cl$.

Preferred conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous MgSO$_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

For pharmaceutical administration, the steroid sulphatase inhibitors of this invention can be formulated in any suitable manner utilising conventional pharmaceutical formulating techniques and pharmaceutical carriers, adjuvants, excipients, diluents etc. and usually for parenteral administration. Approximate effective dose rates are in the range 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

For particular applications, it is envisaged that the steroid sulphatase inhibitors of this invention may be used in combination therapies, either with another sulphatase inhibitor, or, for example, in combination with an aromatase inhibitor, such as for example, 4-hydroxyandrostenedione (4-OHA).

In summation, the present invention provides novel compounds for use as steroid sulphatase inhibitors, and pharmaceutical compositions containing them.

BRIEF DESCRIPTION OF THE DRAWINGS

The present invention will now be described only by way of example with reference to the accompanying drawings in which:

FIG. 1 shows the known structures of oestrone (1), oestrone sulphate (2), EMATE (3) and steroid sulphamates (4–5);

FIG. 2 shows a compound of the Formula I;

FIG. 3 shows a compound of the Formula II;

FIG. 4 shows a compound of the Formula III;

FIG. 5 shows a compound of the Formula IV;

Figure 6:
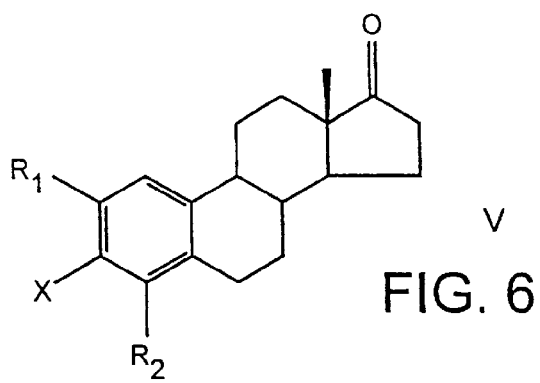
FIG. 6 shows a compound of the Formula V.
Figure 7:
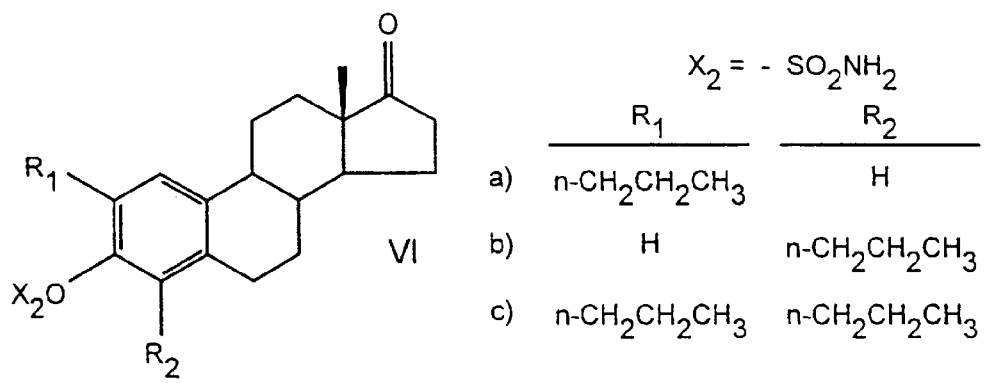
FIG. 7 shows a compound of the Formula VI.
Figure 8:
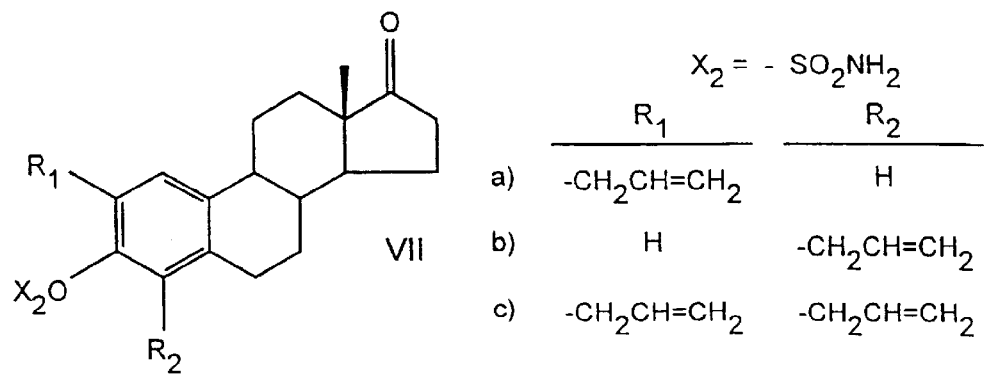
FIG. 8 shows a compound of the Formula VII.
Figure 9:
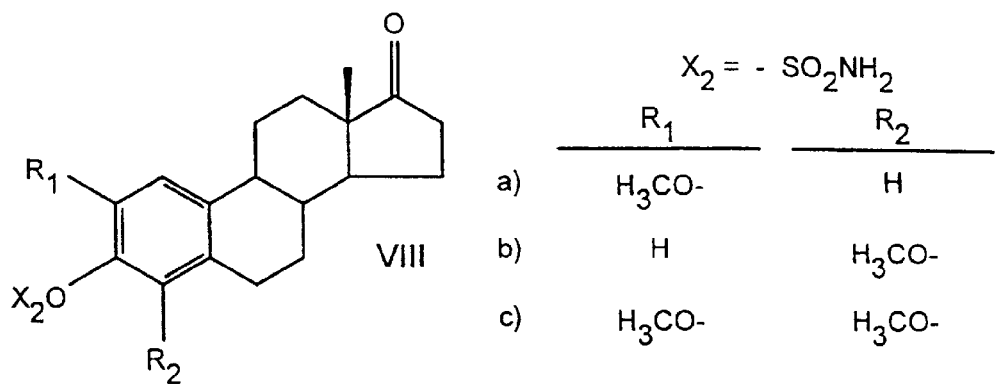
FIG. 9 shows a compound of the Formula VIII.
Figure 10:
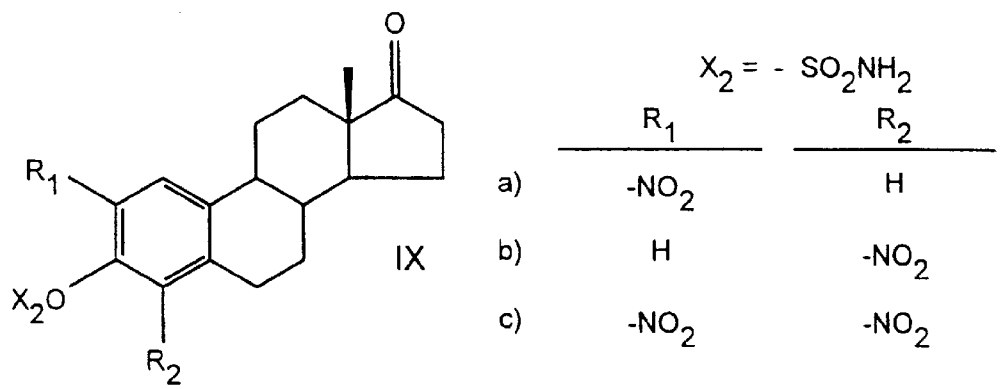
FIG. 10 shows a compound of the Formula IX.
Figure 11:
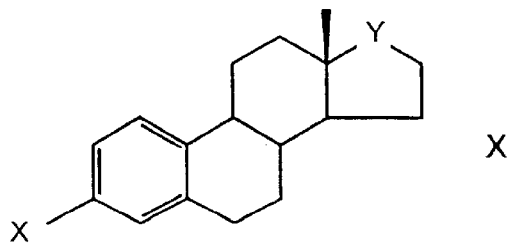
FIG. 11 shows a compound of the Formula X.
Figure 12:
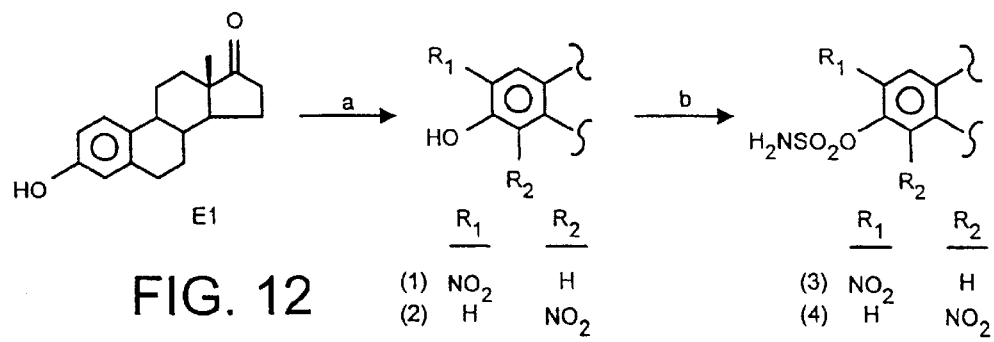
FIG. 12 shows one embodiment of a method of preparing compounds of the present invention.
Figure 13:
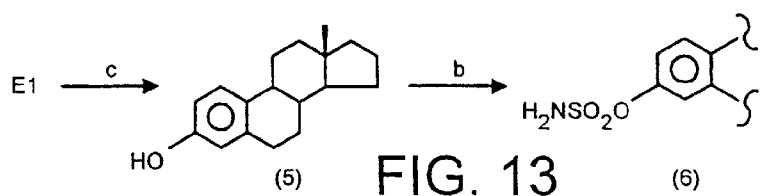
FIG. 13 shows another embodiment of a method of preparing compounds of the present invention.
Figure 14:
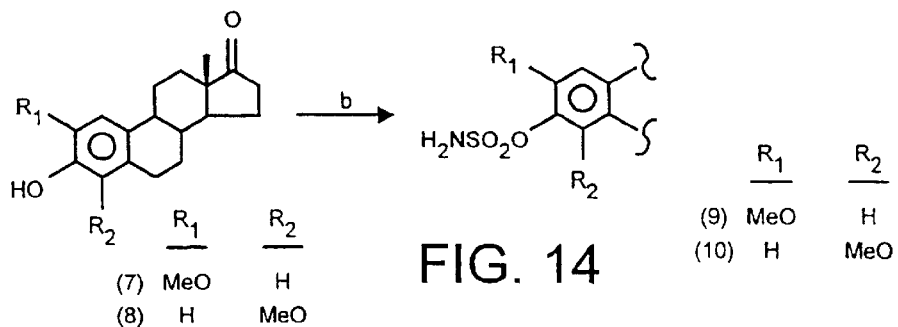
FIG. 14 shows yet another embodiment of a method of preparing compounds of the present invention.
Figure 15:
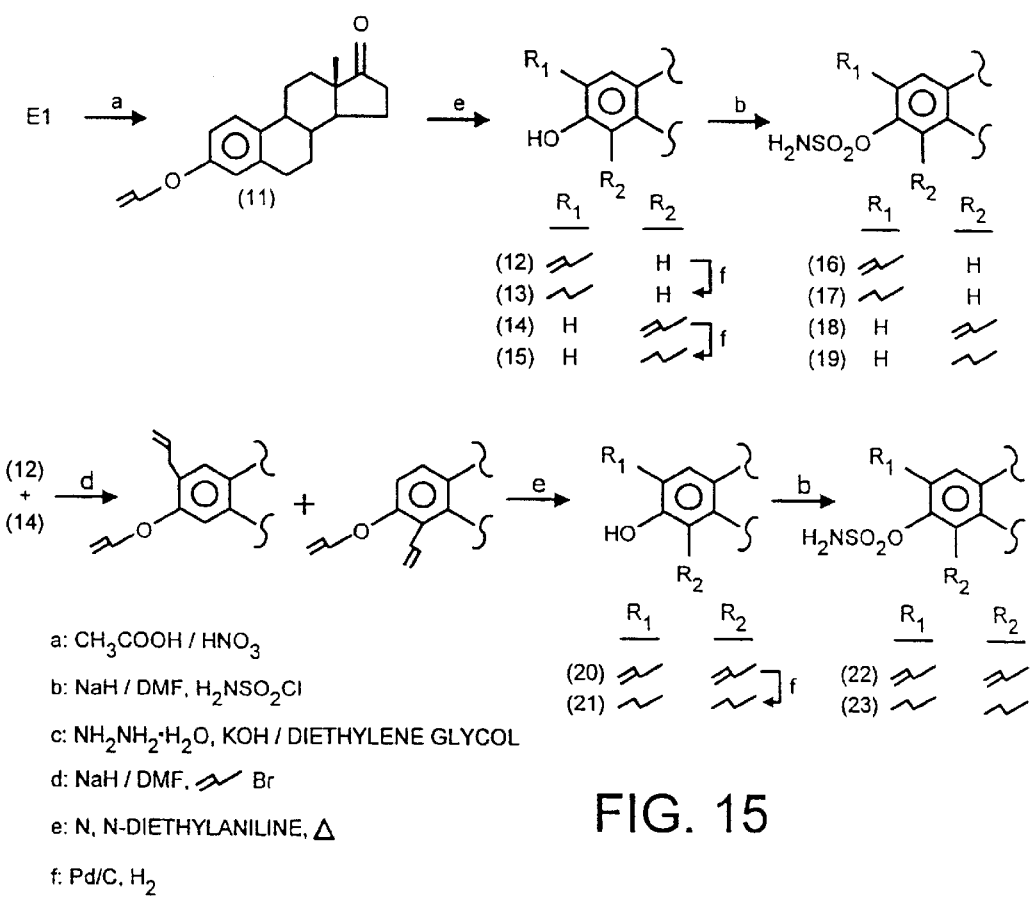
FIG. 15 shows a further embodiment of a method of preparing compounds of the present invention.

The invention will now be described only by way of Examples.

EXAMPLE 1

Preparative Methods

The preparation of various compounds in accordance with the present invention is illustrated in FIGS. 12 to 15. In these Figures, the curved lines attached to the phenyl rings represent the remainder of the ringed structure.

EXAMPLE 2

In Vitro Inhibition

The ability of compounds to inhibit oestrone sulphatase activity was assessed using either intact MCF-7 breast cancer cells or placental microsomes as previously describe[11].

In this regard, the teachings of that earlier reference[11] are as follows:

Inhibition of Steroid Sulphatase Activity in MCF-7 Cells by Oestrone-3-sulphamate Steroid sulphatase is defied as: Steryl Sulphatase EC 3.1.6.2.

Steroid sulphatase activity was measured in vitro using intact MCF-7 human breast cancer cells. This hormone dependent cell line is widely used to study the control of human breast cancer cell growth. It possesses significant steroid sulphatase activity (MacIndoe et al. *Endocrinology*, 123, 1281–1287 (1988); Purohit & Reed, *Int. J. Cancer*, 50, 901–905 (1992)) and is available in the U.S.A. from the American Type Culture Collection (ATCC) and in the U.K. (e.g. from The Imperial Cancer Research Fund). Cells were maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm$^2$ tissue culture flasks were seeded with approximately 1×10$^5$ cells/flask using the above medium. Cells were grown to 80% confluency and medium was changed every third day.

Intact monolayers of MCF-7 cells in triplicate 25 cm$^2$ tissue culture flasks were washed with Earle's Balanced Salt Solution (EBSS from ICN Flow, High Wycombe. U.K.) and incubated for 3–4 hours at 37° C. with 5 pmol (7×10$^5$ dpm) [6,7-$^3$H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask was cooled and the medium (1 ml) was pipetted into separate tubes containing [$^{14}$C] oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$] oestrone and <0.1 % [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate. Each batch of experiments included incubations of microsomes prepared from a sulphatase-positive human placenta (positive control) and flasks without cells (to assess apparent non-enzymatic hydrolysis of the substrate). The number of cell nuclei per flask was determined using a Coulter Counter after treating the cell monolayers with Zaponin. One flask in each batch was used to assess cell membrane status and viability using the Trypan Blue exclusion method (Phillips, H. J. (1973) In: *Tissue culture and applications*, [eds: Kruse, D. F. & Patterson, M. K.]; pp. 406–408; Academic Press, New York).

Results for steroid sulphatase activity are expressed as the mean ±1 S.D. of the total product (oestrone+oestradiol) formed during the incubation period (20 hours) calculated for 10$^6$ cells and, for values showing statistical significance, as a percentage reduction (inhibition) over incubations containing no oestrone-3-sulphamate. Unpaired Student's t-test was used to test the statistical significance of results.

Inhibition of Steroid Sulphatase Activity in Placental Microsomes by Oestrone-3-sulphamate Sulphatase-positive human placenta from normal term pregnancies (Obstetric Ward, St. Mary's Hospital, London) were thoroughly minced with scissors and washed once with cold phosphate buffer (pH 7.4, 50 mM) then re-suspended in cold phosphate buffer (5 ml/g tissue). Homogenisation was accomplished with an Ultra-Turrax homogeniser, using three 10 second bursts separated by 2 minute cooling periods in ice. Nuclei and cell debris were removed by centrifuging (4° C.) at 2000 g for 30 minutes and portions (2 ml) of the supernatant were stored at −20° C. The protein concentration of the supernatants was determined by the method of Bradford (*Anal. Biochem.*, 72, 248–254 (1976)).

Incubations (1 ml) were carried out using a protein concentration of 100 mg/ml, substrate concentration of 20 mM [6,7-$^3$H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample was cooled and the medium (1 ml) was pipetted into separate tubes containing [14C]oestrone (7×10$^3$ dpm) (specific activity 97 Ci/mmol from Amersham International Radiochemical Centre, Amersham, U.K.). The mixture was shaken thoroughly for 30 seconds with toluene (15 ml). Experiments showed that >90% [$^{14}$C]oestrone and <0.1% [$^3$H] oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C] oestrone added) and the specific activity of the substrate.

For the present invention, the percentage inhibition for the series of EMATE analogues tested in either MCF-7 cells or placental microsomes is shown in Table 1.

EXAMPLE 2

In Vivo Studies

Using 17-deoxy oestrone-3-O-sulphamate (NOMATE, FIG. 5, Formula IV where X=—OSO$_2$NH$_2$, Y=—CH$_2$— and R$_1$ and R$_2$=H, and FIG. 13) as a representative example, the ability of this compound to inhibit oestrone sulphatase activity in vivo was examined in rats. The oestrogenicity of this compound was examined in ovariectomised rats. In this model compounds which are oestrogenic stimulate uterine growth.

(i) Inhibition of Oestrone Sulphatase Activity in vivo

NOMATE (0.1 mg/Kg/day for five days) was administered orally to rats with another group of animals receiving vehicle only (propylene glycol). At the end of the study samples of liver tissue were obtained and oestrone sulphatase activity assayed using $^3$H oestrone sulphate as the substrate as previously described[11].

Figure 16:
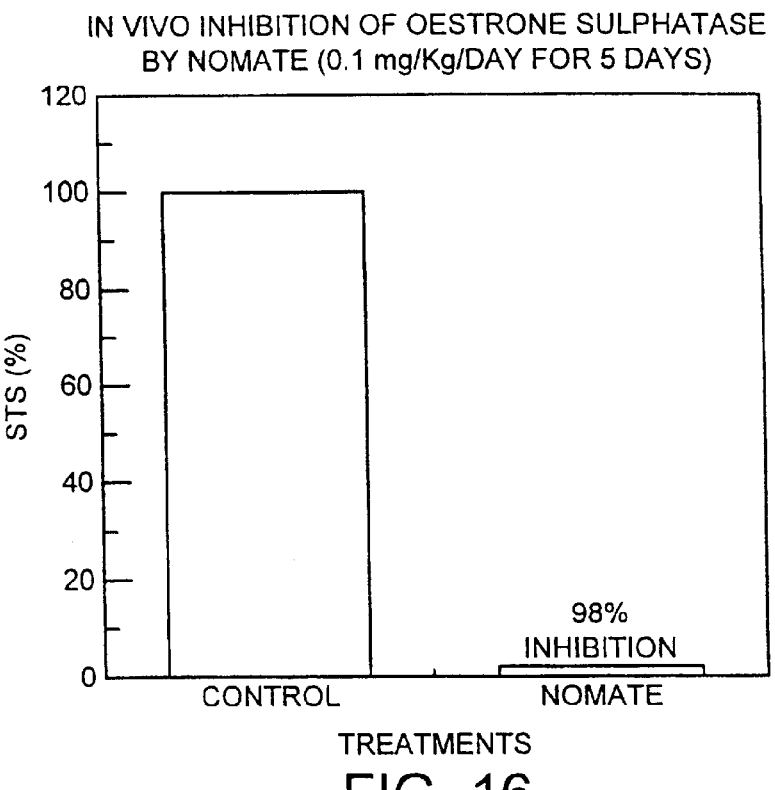
FIG. 16 shows a graph illustrating the in vivo inhibition of oestrone sulphatase by NOMATE (0.1 mg/Kg/day for five days)

As shown in FIG. 16, administration of this dose of NOMATE effectively inhibited oestrone sulphatase activity by 98% compared with untreated controls.

(ii) Lack of in vivo Oestrogenicity

NOMATE (0.1 mg/Kg/day for five days) was administered orally to rats with another group of animals receiving vehicle only (propylene glycol). At the end of the study uteri were obtained and weighed with the results being expressed as uterine weight/whole body weight×100.

Figure 17:
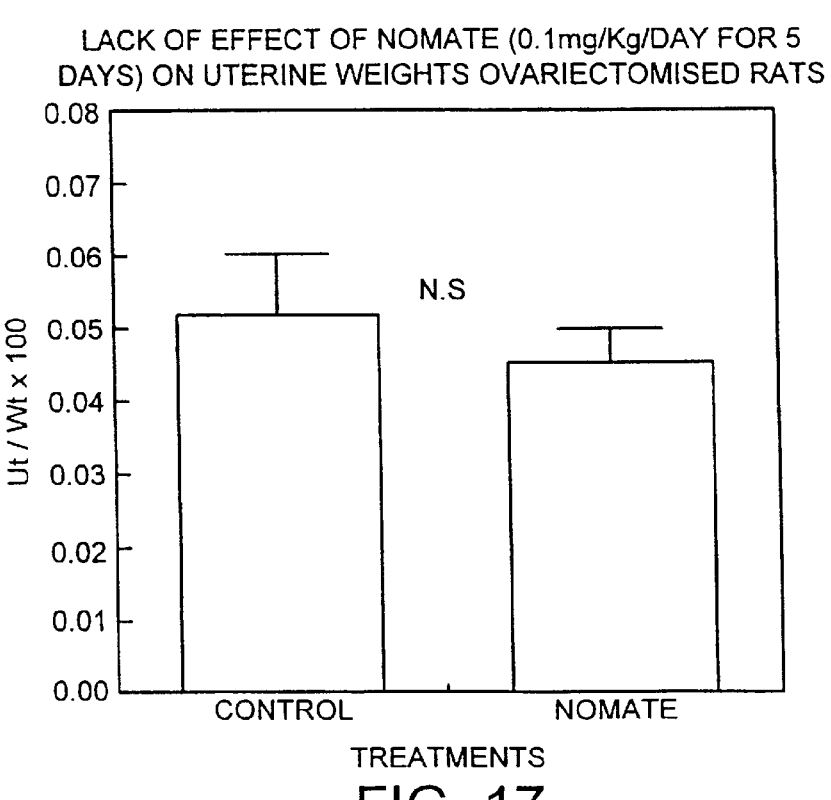
FIG. 17 shows a graph illustrating the lack of effect of NOMATE (0.1 mg/Kg/day for five days) on uterine weights in ovariectomised rats.

As shown in FIG. 17, administration of NOMATE at the dose tested, but had no significant effect on uterine growth, showing that at this dose the compound is not oestrogenic.

TABLE 1

Inhibition of Oestrone Sulphatase Activity in MCF-7 Cells or Placental Microsomes by EMATE Analogues

| | | % Inhibition (Mean) | |
| --- | --- | --- | --- |
| Inhibitor | Concentration Tested (mM) | MCF-7 Cells | Placental Microsomes |
| 2-n-propyl EMATE | 0.1 | 41.1 | — |
| | 1 | 83.1 | 21.9 |
| | 10 | 92.2 | 43.2 |
| | 25 | — | 47.5 |
| | 50 | — | 61.1 |
| | 100 | — | 69.2 |
| 4-n-propyl EMATE | 1 | — | 13.7 |
| | 10 | — | 10.2 |
| | 25 | — | 15.7 |
| | 50 | — | 16.3 |
| | 100 | — | 23.7 |
| 2,4-n-dipropyl EMATE | 0.1 | 6.6 | — |
| | 1 | 10.6 | — |
| 2-allyl EMATE | 0.01 | 23.2 | — |
| | 0.1 | 76.1 | — |
| | 1 | 94.2 | 45.6 |

TABLE 1-continued

Inhibition of Oestrone Sulphatase Activity in MCF-7 Cells or Placental Microsomes by EMATE Analogues

| Inhibitor | Concentration Tested (mM) | % Inhibition (Mean) MCF-7 Cells | % Inhibition (Mean) Placental Microsomes |
|---|---|---|---|
|  | 10 | 93.7 | 65.4 |
|  | 25 | — | 75.3 |
|  | 50 | — | 86.6 |
|  | 100 | — | 89.6 |
| 4-allyl EMATE | 1 | — | 29.1 |
| (approx 75%) | 10 | — | 54.2 |
|  | 25 | — | 59.0 |
|  | 50 | — | 65.1 |
|  | 100 | — | 71.9 |
| 2,4-di-allyl EMATE | — | — | — |
| 2-methoxy EMATE | 0.1 | 96.0 | — |
|  | 1 | 93.6 | — |
|  | 10 | 96.2 | 99.0 |
|  | 50 | — | 99.7 |
|  | 100 | — | 99.7 |
| 2-nitro EMATE | 0.05 | — | 44.5 |
|  | 0.5 | — | 93.9 |
|  | 5 | — | 99.0 |
|  | 50 | — | 99.4 |
| 4-nitro EMATE | 20 | — | 99.0 |
| NOMATE | 0.1 | 96.4 | 97.2 |
| (17-deoxy EMATE) | 1 | 99.1 | 99.5 |
|  | 10 | 99.7 | 99.5 |
|  | 25 | 99.7 | 99.7 |

— = not tested
Irreversible time- and concentration-dependent inhibition is assumed for these compounds in keeping with established precedent[8].

Other modifications of the present invention will be apparent to those skilled in the art.

REFERENCES (1) Santner, S. J.; Feil, P. D.; Santen, R. J. In situ oestrogen production via the oestrone sulphatase pathway in breast tumors: relative importance vs. the aromatase pathway. *J. Clin. Endocrinol. Metab.* 1984, 59, 29–33.
(2) Yamamoto, T.; Kitawaki, J.; Urabe, M.; Honjo, H.; Tamura, T.; Noguchi, T.; Okada, H.; Sasaki, H.; Tada, A.; Terashima, Y.; Nakamura, J.; Yoshihama, M. Oestrogen productivity of endometrium and endometrial cancer tissue—influence of aromatase on proliferation of endometrial cancer cells. *J. Steroid Biochem. Mot. Biol.* 1993, 44, 463468.
(3) Santen, R. J.; Santner, S. J.; Davis, B.; Veldhuis, I.; Samojilik, E.; Ruby, E. Aminogluthethimide inhibits extraglandular oestrogen production in post-menopausal women with breast carcinoma. *J. Clin. Endocrinol. Metab.* 1978, 47, 1257–1265.
(4) Reed, M. J.; Lai, L. C.; Owen, A. M.; Singh, A.; Coldham, N. G.; Purohit, A.; Ghilchik, M. W.; Shaikh, N. A.; James, V. H. T. Effect of treatment with 4-hydroxy-androstenedione on the peripheral conversion of androstenedione to oestrone and in vitro tumour aromatase activity in postmenopausal women with breast cancer. *Cancer Res.* 1990, 50, 193–196.
(5) Ruder, H. J.; Loriaux, D. L.; Lipsett, M. B. Oestrone sulphate: production rate and metabolism in man. *J. Clin. Invest.* 1972, 51, 1020–1023.
(6) James, V. H. T.; McNeill, J. M.; Lai, L. C.; Newton, C. J.; Ghilchik, M. W.; Reed, M. J. Aromatase activity in normal breast and breast tumor tissues: in vivo and in vitro studies. *Steroids* 1987, 50, 269–279.
(7) Howarth, N. M.; Purohit, A.; Reed, M. J.; Potter, B. V. L. Oestrone sulphamates: potent inhibitors of oestrone sulphatase with therapeutic potential. *J. Med. Chem.* 1994, 37, 219–221.
(8) Purohit, A.; Williams, G. J.; Howarth, N. M.; Potter, B. V. L.; Reed, M. J. Inactivation of steroid sulphatase by an active site-directed inhibitor, oestrone-3-O-suiphamate. *Biochemistry* 1995, 34, 11508–11514.
(9) Purohit, A.; Dauvois, S.; Parker, M. G.; Potter, B. V. L.; Williams, G. J.; Reed, M. J. The hydrolysis of oestrone sulphate and dehydroepiandrosterone sulphate by human steroid sulphatase expressed in transfected COS-1 cells. *J. Steroid Biochem. Mot. Biol.* 1994, 50, 101–104.
(10) Dauvois, S.; Labrie, F. Androstenedione and androst-5-ene-3b,17bdiol stimulate DMBA-induced rat mammary tumours—role of aromatase. *Breast Cancer Res. Treat.* 1989, 13, 6169.
(11) Purohit, A.; Williams, G. J.; Roberts, C. J.; Potter, B. V. L.; Reed, M. J. In vivo inhibition of oestrone sulphatase and dehydroepiandrosterone sulphatase by oestrone-3-O-sulphamate. *Int. J. Cancer* 1995, 62, 106–111.
(12) Woo, L. W. L.; Lightowler, M.; Purohit, A.; Reed, M. J.; Potter, B. V. L. Heteroatom-substituted analogues of the active-site directed inhibitor oestra-1,3,5(10)-trien-17-one-3-sulphamate inhibit oestrone sulphatase by a different mechanism. *J. Steroid Biochem. Mol. Biol.* 1996 (in press).
(10) Elger, W.; Schwarz, S.; Hedden, A.; Reddersen, G.; Schneider, B. Sulphamates of various oestrogens—prodrugs with increased systemic and reduced hepatic oestrogenicity at oral application. *J. Steroid Biochem. Mol. Biol.* 1995, 55, 395403.
(14) Li, P. K; Rhodes, M. E.; Jagannathan, S; Johnson, D. A. Memory enhancement mediated by the steroid sulphatase inhibitor oestrone 3-O-sulphamate. *J. Endocrinol.* 1995, 144, Abstr. P155.
(15) Daynes, R. A.; Araneo, B. A.; Dowell, T. A.; Huang, K.; Dudley, D. Regulation of murine lymphokine production in vivo. 3. The lymphoid tissue micro-environment exerts regulatory influences over T-helper cell function. *J. Exp. Med.* 1990, 171, 979–996.
(16) Rook, G. A. W.; Hernandez-Pando, R.; Lightman, S. Hormones, peripherally activated prohormones and regulation of the TH1/TH2 balance. *Immunol. Today* 1994, 15, 301–303.

What is claimed is:

1. A method for inhibiting oestrone sulphatase without administering an oestrogenic compound in a subject in need thereof comprising administering to said subject a sulphamate compound having the Formula (X) and wherein X is a sulphamate group, and Y is $CH_2$ and none of the other H atoms attached directly to the ring system is substituted by another group

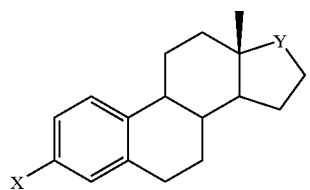

(X)

and wherein the compound is non-oestrogenic in a uterine growth test.

2. The method for inhibiting oestrone sulphatase without administering an oestrogenic compound in a subject in need thereof as claimed in claim 1, wherein the sulphamate group, X, has the Formula (III); wherein each of $R_3$ and $R_4$ is independently selected from H, alkyl, cycloalkyl, alkenyl and aryl, or together represent alkylene optionally containing one or more hetero atoms or groups in the alkylene chain

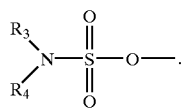
(III)

3. The method for inhibiting oestrone sulphatase without, administering an oestrogenic compound in a subject in need thereof as claimed in claim 2 wherein in Formula (III), at least one of $R_3$ and $R_4$ is H.

4. The method for inhibiting oestrone sulphatase without administering an oestrogenic compound in a subject in need thereof as claimed in claim 3 wherein in Formula (III), each of $R_3$ and $R_4$ is H.

* * * * *